US012472080B2

(12) United States Patent
Kartalov

(10) Patent No.: US 12,472,080 B2
(45) Date of Patent: Nov. 18, 2025

(54) SCALABLE MICROFLUIDIC DOUBLE-HELIX WEAVE ARCHITECTURE FOR 3D-PRINTABLE BIOMIMETIC ARTIFICIAL MUSCLES

(71) Applicant: THE UNITED STATES OF AMERICA, AS REPRESENTED BY THE SECRETARY OF THE NAVY, Arlington, VA (US)

(72) Inventor: Emil Paskalev Kartalov, Pacific Grove, CA (US)

(73) Assignee: The Government of the United States of America, as represented by the Secretary of the Navy, Arlington, VA (US)

( * ) Notice: Subject to any disclaimer, the term of this patent is extended or adjusted under 35 U.S.C. 154(b) by 787 days.

(21) Appl. No.: 17/845,989

(22) Filed: Jun. 21, 2022

(65) Prior Publication Data

US 2022/0401235 A1 Dec. 22, 2022

Related U.S. Application Data

(60) Provisional application No. 63/213,178, filed on Jun. 21, 2021.

(51) Int. Cl.

*A61F 2/74* (2006.01)
*A61F 2/50* (2006.01)

(52) U.S. Cl.

CPC ................ *A61F 2/741* (2021.08); *A61F 2/74* (2021.08); *A61F 2002/5066* (2013.01)

(58) Field of Classification Search

CPC .......... A61F 2/741; A61F 2/74; A61F 2/5044; A61F 2002/5066; A61F 2002/0894
USPC ............................................................ 623/26
See application file for complete search history.

(56) References Cited

U.S. PATENT DOCUMENTS

2011/0227455 A1* 9/2011 Nagamitsu ............. B25J 9/1095 310/333

OTHER PUBLICATIONS

Kartalov, Emil. "Consortium for Robotics and Unmanned Systems Education and Research (Cruser) 2019 Annual Report." Naval Postgraduate School, Feb. 28, 2020. p. 52-55 (Year: 2020).*

(Continued)

*Primary Examiner* — Jerrah Edwards
*Assistant Examiner* — Gabriella G Rios
(74) *Attorney, Agent, or Firm* — Heber Martin Carbajal Chavez; Scott Bell

(57) ABSTRACT

A double-helix weave architecture for an artificial muscle is described. The artificial muscle includes a number of microfluidic channels that are arranged into artificial muscles fibers, where each artificial muscle fiber includes two independent mutually-unconnected microfluidic channels that are entwined in a double helix weave and maintained at opposite electrical polarity.

14 Claims, 5 Drawing Sheets
(5 of 5 Drawing Sheet(s) Filed in Color)

(56) References Cited

OTHER PUBLICATIONS

J. Zhang, J. Sheng, C.T. O'Neill, C.J. Walsh, R.J. Wood, J.H. Ryu, J.P. Desai, and M.C. Yip, IEEE Transactions on Robotics, 2019, 35 (3), p. 761.
Y. Bahramzadeh and M. Shahinpoor, Soft Robot, 2014, 1 (1), pp. 38-52.
H. Yin, J. Zhou, J. Li, and V.S. Joseph, JEMEPEG 27:3581-3589 (2018).
M. Kim, G.Y. Lee, C.S. Kim, and S.N. Ahn, Small: Nano Micro. 14(23) (2018).
F.Q. Hu, Y. Xue, J.K. Xu, and B.Y. Lu, Frontiers in Robotics and AI 6, #114 (2019).

* cited by examiner

SCALABLE MICROFLUIDIC DOUBLE-HELIX WEAVE ARCHITECTURE FOR 3D-PRINTABLE BIOMIMETIC ARTIFICIAL MUSCLES

CROSS-REFERENCE TO RELATED APPLICATIONS

This patent application is a non-provisional of and claims the benefit of U.S. Provisional application 63/213,178, filed Jun. 21, 2021, which is hereby incorporated by reference in its entirety.

BACKGROUND OF THE INVENTION

1. Field of the Invention

The present disclosure relates to microcapacitor arrays in general, and, more particularly, to a double-helix weave architecture for wiring of microcapacitor arrays in artificial muscles.

2. Description of the Related Art

Traditional robotic actuation is done via electric motors or pneumatics/hydraulics. Electromagnetic step motors offer precision, use a convenient form of power, and have some capability for miniaturization, making them the usual choice for small robots and prosthetics. However, these motors are actually electromagnetic (EM) motors, which require a strong magnetic field generated either by strong permanent magnets or solenoids running large currents. Conventional EM motors often choose the latter path and require significant power to operate, while generating excess heat.

Pneumatic systems provide more force in large systems, e.g., construction vehicles, industrial assembly lines, the US Army's Mule walking robot, etc., but they require compressors, an spring leaks, and output less force when scaled down for use in compact systems. Furthermore, complex fluid motions are difficult to achieve by pneumatics because pressure is typically either on or off, producing jerky choppy motion that may be acceptable in an industrial robot but impractical in exoskeletons, prosthetics, etc.

Due to these limitations, a wide range of applications requiring actuation, such as exoskeletal locomotion, walking robots, biomimetic underwater propulsion, prosthetics, medical servo-assists, and small-scale biomimetic robots, look to different actuation systems as a potential solution, including artificial muscles. Artificial muscles can be organized in several large groups: piezoelectrics, pneumatic artificial muscles (PAM), thermal actuators, and electroactive polymers (EAP).

SUMMARY OF THE INVENTION

Embodiments described herein related to a double-helix weave architecture for an artificial muscle. In some cases, the artificial muscle includes a number of microfluidic channels that are arranged into artificial muscles fibers, where each artificial muscle fiber includes two independent mutually-unconnected microfluidic channels that are entwined in a double helix weave and maintained at opposite electrical polarity.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a more complete understanding of the present disclosure, reference is now made to the following descriptions taken in conjunction with the accompanying drawings, in which.

DETAILED DESCRIPTION OF THE INVENTION

The following description is provided to enable any person skilled in the art to use the invention and sets forth the best mode contemplated by the inventor for carrying out the invention. Various modifications, however, will remain readily apparent to those skilled in the art since the principles of the present invention are defined herein specifically to provide microcapacitor arrays for artificial muscles.

Related patent applications described artificial muscles based on a combination of microfluidics, electrostatic actuation, liquid electrodes, and 3D-printing. Briefly, arrays of microcapacitor stacks defined microfluidically and connected in parallel can produce a longitudinal contractive force density that scales as the square of applied voltage and the inverse square of the distance between the microcapacitor plates. COMSOL simulations predict up to 33 MPa force density at current extreme limits of manufacture and materials. While these muscles boast high promise and utility, a major problem remains to be solved, i.e. how to connect and organize the microcapacitor arrays fluidically and electrically in a scalable fashion that also allows reliable loading of the liquid/gel electrodes. Embodiments herein describe an innovative solution for the needed large-scale microfluidic architecture.

The basic problem of wiring the microcapacitor arrays stems from microfluidic, mechanical, electrical, and scaling restrictions, with the added challenge that all such must be satisfied simultaneously for the architecture to be functional and practicable.

From a mechanical perspective, the microcapacitors should be arranged in columns, so that their individual microscopic contractions add up to a macroscopic elongation along the longitudinal direction of the device, to produce the required length of motion during actuation. Furthermore, the individual columns of stacked microcapacitors must be arranged in parallel to the longitudinal direction and arrayed laterally in the remaining two orthogonal dimensions. This ensures that the columns contract in parallel and the generated forces add constructively to output a cumulative force to the macroscale world.

Figure 2:
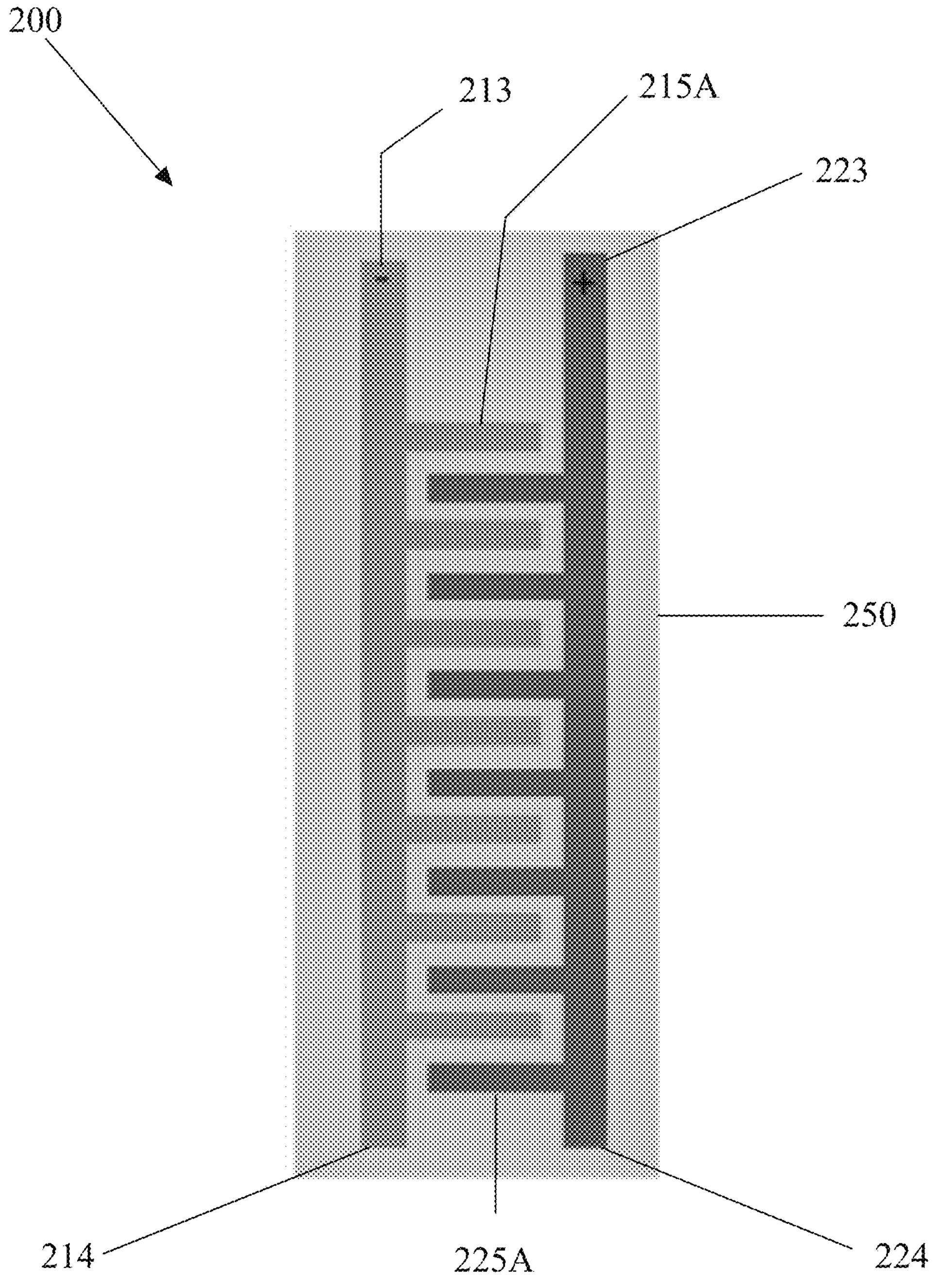
FIG. 2 is an illustration of an artificial muscle fiber within bulk structural material.

As a third requirement, the bulk material, as shown in FIG. 2, such as but not limited to a polymer between adjacent columns should be as monolithic and mechanically strong as possible, since it would serve as a tendon equivalent. In biological muscles, the individual fibers are grouped in bundles while their sheathing is made of connective tissue that becomes the tendons by which the muscle attaches to the bones. As the biological muscle fibers contract, they pull on the tendons, which transfer the generated force to the outside world. Similarly, the microcapacitor stacks convey their contraction to the surrounding bulk material, which acts as tendon and transfers a portion of the generated force to the outer macroscale world. The tendon would be strongest if there are as few disruptions as possible in the lateral directions. So, any channel serving as wiring inside the structure should be ideally precluded from running perpendicular to the tendons as it would weaken them structurally. The periodicity in the design should reflect that as well.

From electrical perspective, each microcapacitor is a set of two plates of opposite polarity, so each plate should be connected to an outside electrode of the respective polarity. Because the microcapacitors are stacked in columns, this means the polarity should alternate along each column, from plate to adjacent plate. The simplest design to achieve this is two combs kept at opposite polarity and facing each other with their prongs interdigitated. This would work electrically but produces a fluidic problem: The prongs are dead-end channels which would be difficult to fill with conducting fluid.

If the matrix of the polymer is permeable to air (e.g. silicone), this can be done by dead-end priming, but 3D printing is done in resin, which in general would have very low permeability to air. With dead-end priming not an option, it is necessary to have a through-channel to ensure proper air evacuation as the conducting fluid fills the channel. Moreover, fluidic resistance would not be constant along all prongs, which can produce shunts and resulting filling problems. To avoid that, each comb can be replaced with a binary-tree architecture, but that significantly increases the complexity as well as the vascularity in the lateral direction, thereby weakening the tendons and contradicting a major mechanical requirement.

Artificial muscle fiber 100 may be a double helix weave constructed by first helix 110 and second helix 120. First helix 110 may include multiple microfluidic channels 111 and 112, and multiple microcapacitor plates 115A and 115B having a first polarity. Second helix 120 may include multiple microfluidic channels 121 and 122, and multiple microcapacitor plates 125A and 125B having a second polarity.

Figure 1A:
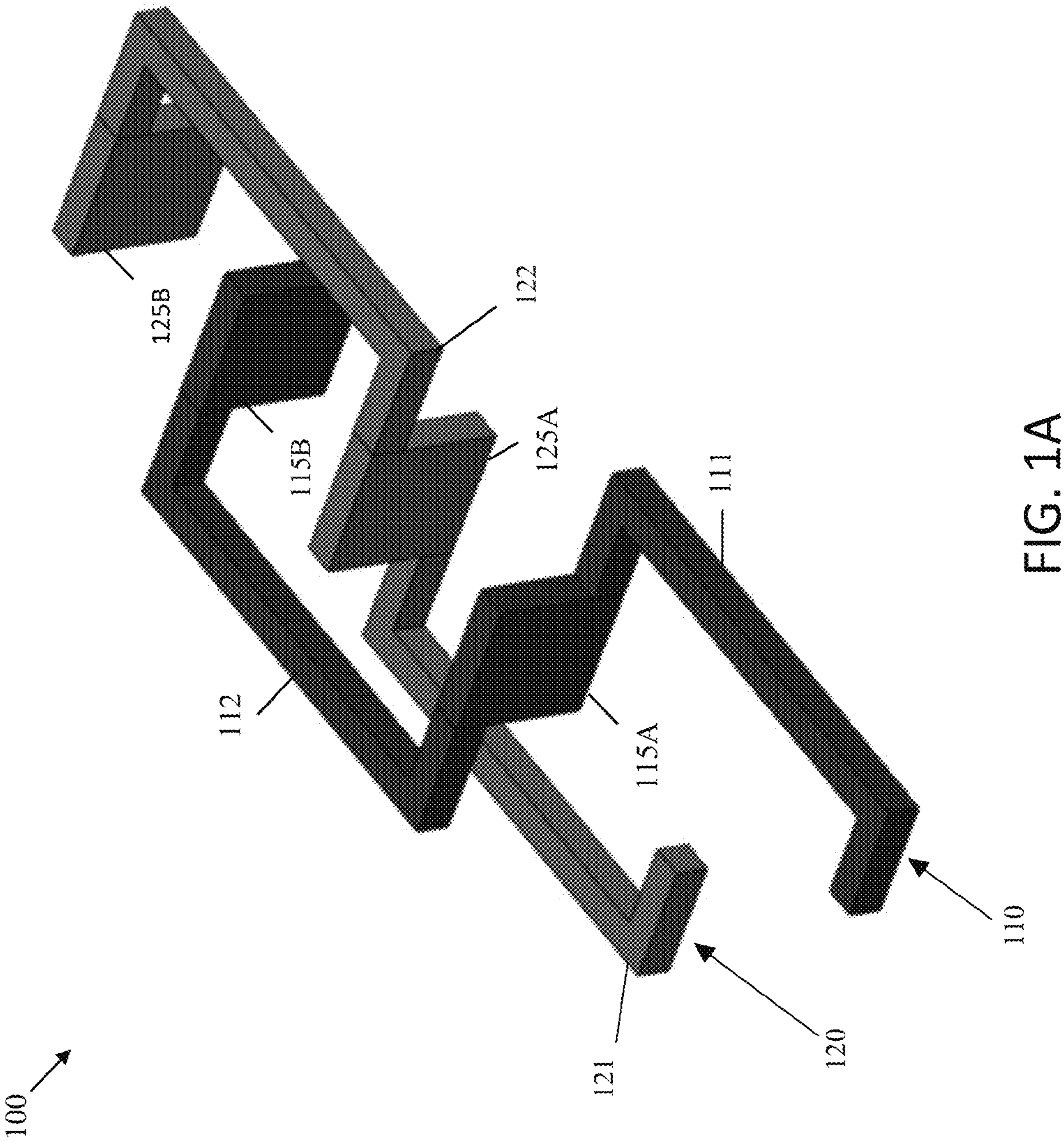
FIGS. 1A-1D show a scalable weave architecture for artificial muscles in accordance with embodiments described herein.

To ensure proper evacuation and avoid tendon weakening, the wiring should be done in the longitudinal direction with longitudinal periodicity and no dead ends. This means each microcapacitor plate 115A, 115B, 125A, and 125B should be accessed by connecting a microfluidic input and a microfluidic output ideally at opposite corners with microfluidic channels 111, 112, 121, and 122, as shown in FIG. 1A. It stands to reason that if one polarity uses top left and bottom right, as shown in FIG. 1A, then the other should use bottom left and top right. This logic derives artificial muscle fiber 100.

Figure 1B:
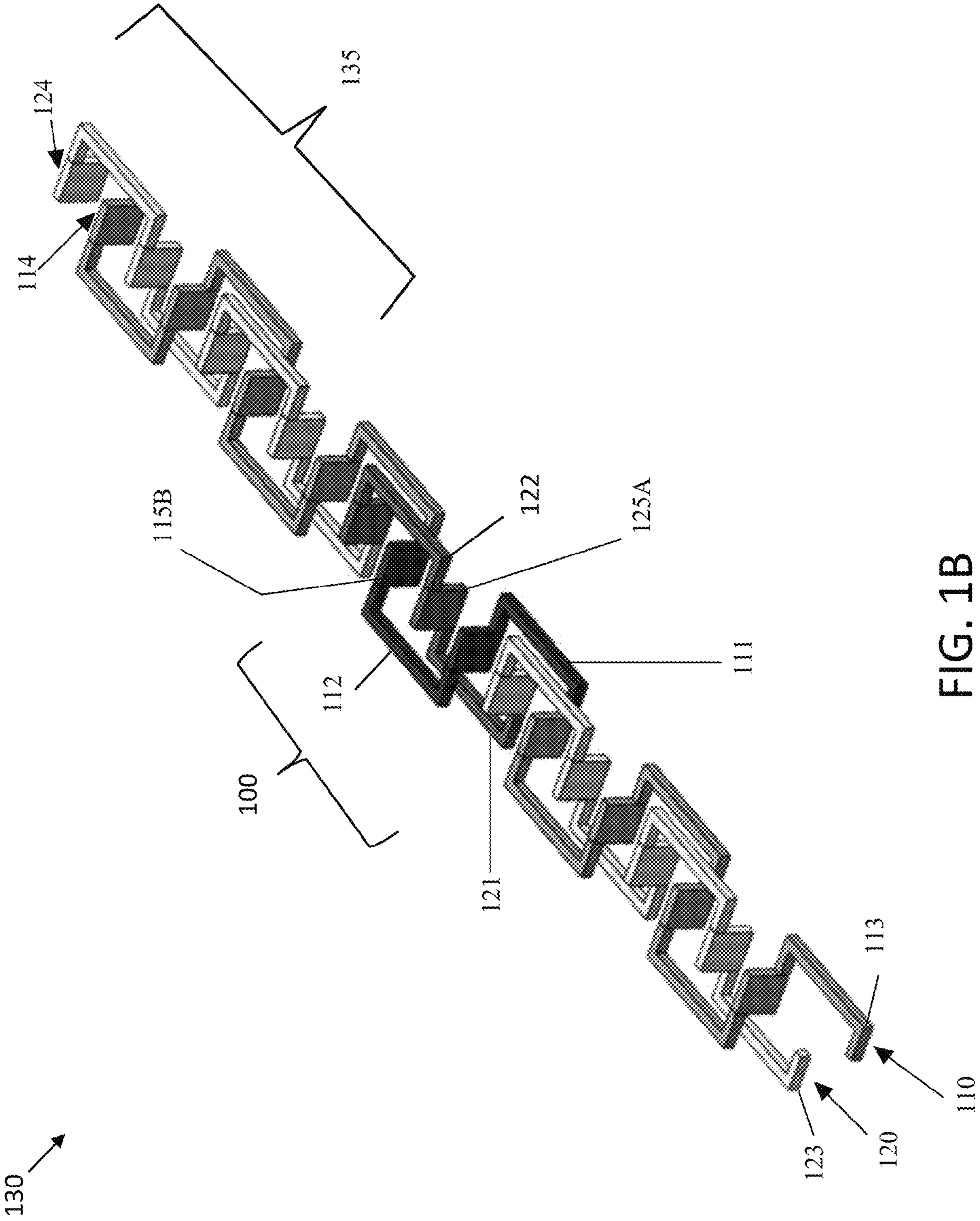

Artificial muscle fiber 100 may be an array of N artificial muscle fibers 135 formed on a longitudinal axis to produce the structure of a single muscle fiber 130 as shown in FIG. 1B. Curiously, the resulting weave is a double helix akin to dsDNA. The polarity of first helix 120 and second helix 110 never cross but connect to alternating plates along the column of microfluidic channel 111, 112, 121, and 122. There may be a first polarity input 113 and a second polarity input 123 and a first polarity output 114 and a second polarity output 124 regardless of the length of artificial muscle fiber 130. Also, first helix 110 and second helix 120 are each a cmicrofluidic channel formed by microfluidic channels 111, 112, 121, and 122 and microcapacitors plates 115A, 115B, 125A, and 125B, greatly facilitating reliable filling with conducting fluid.

Figure 1C:
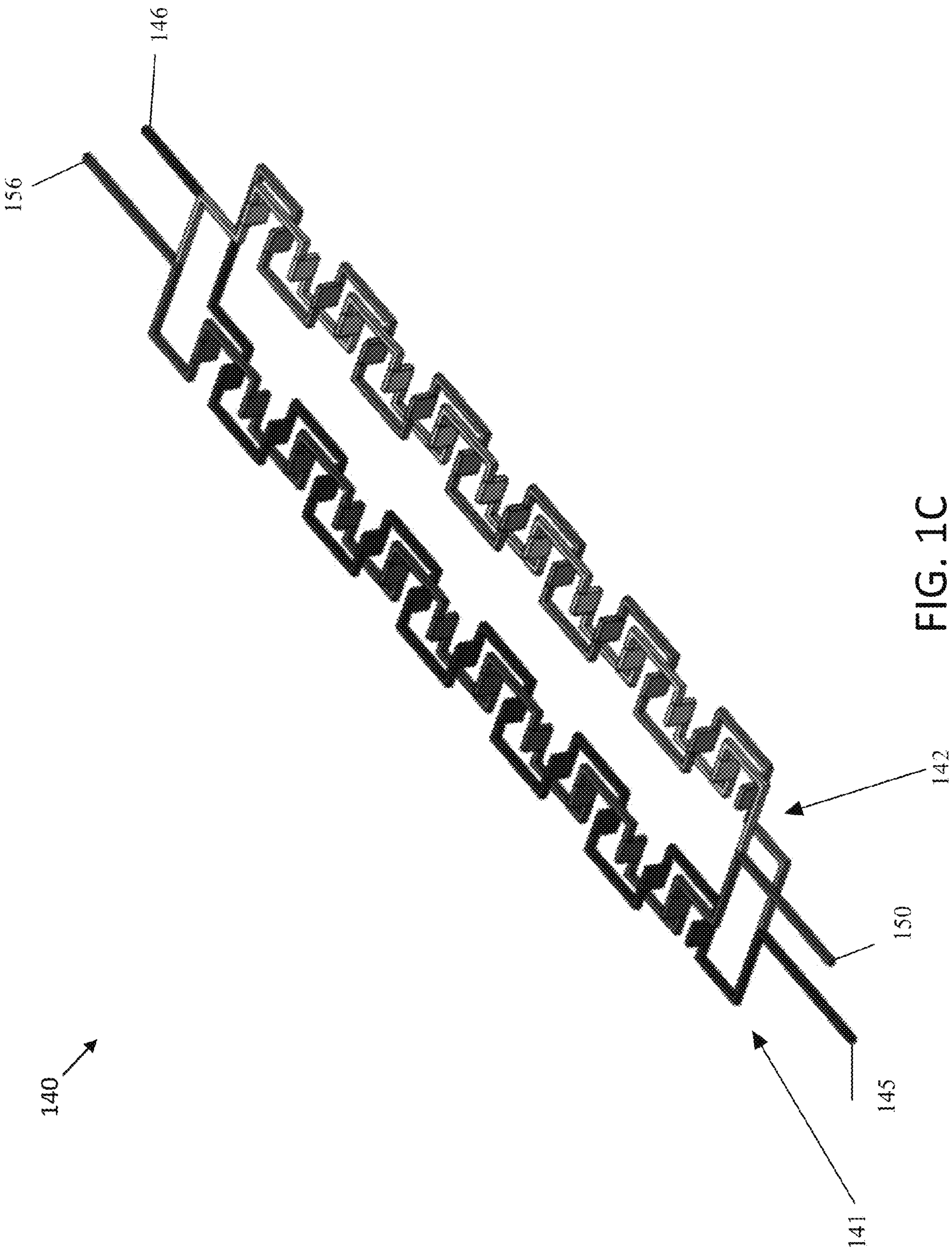

Mechanical considerations dictate a limit to the aspect ratio between plate width and plate thickness. Excessive aspect ratio can lead to plate collapse and improper filling. That would degrade electrical performance since it would decrease the electrode area and capacitance, leading to diminished charge and force at the same voltage. Furthermore, force transfer to the tendon ought to be more efficient with smaller plates 103A-D. As a result, the optimal design should be a bundle of a large number of thin parallel fibers arrayed laterally. Also, such fibers should be wired together in a scalable fashion. The solution is again microfluidic and based on a binary tree. FIG. 1C shows a pair of artificial muscle fibers 141 and 142 wired in a binary fashion. The symmetry of the design ensures theoretically equal fluidic resistance from first input 145 to first output 146 and second input 150 to second output 156 for each polarity. This should help achieve easy and reliable filling with no shunts.

Figure 1D:
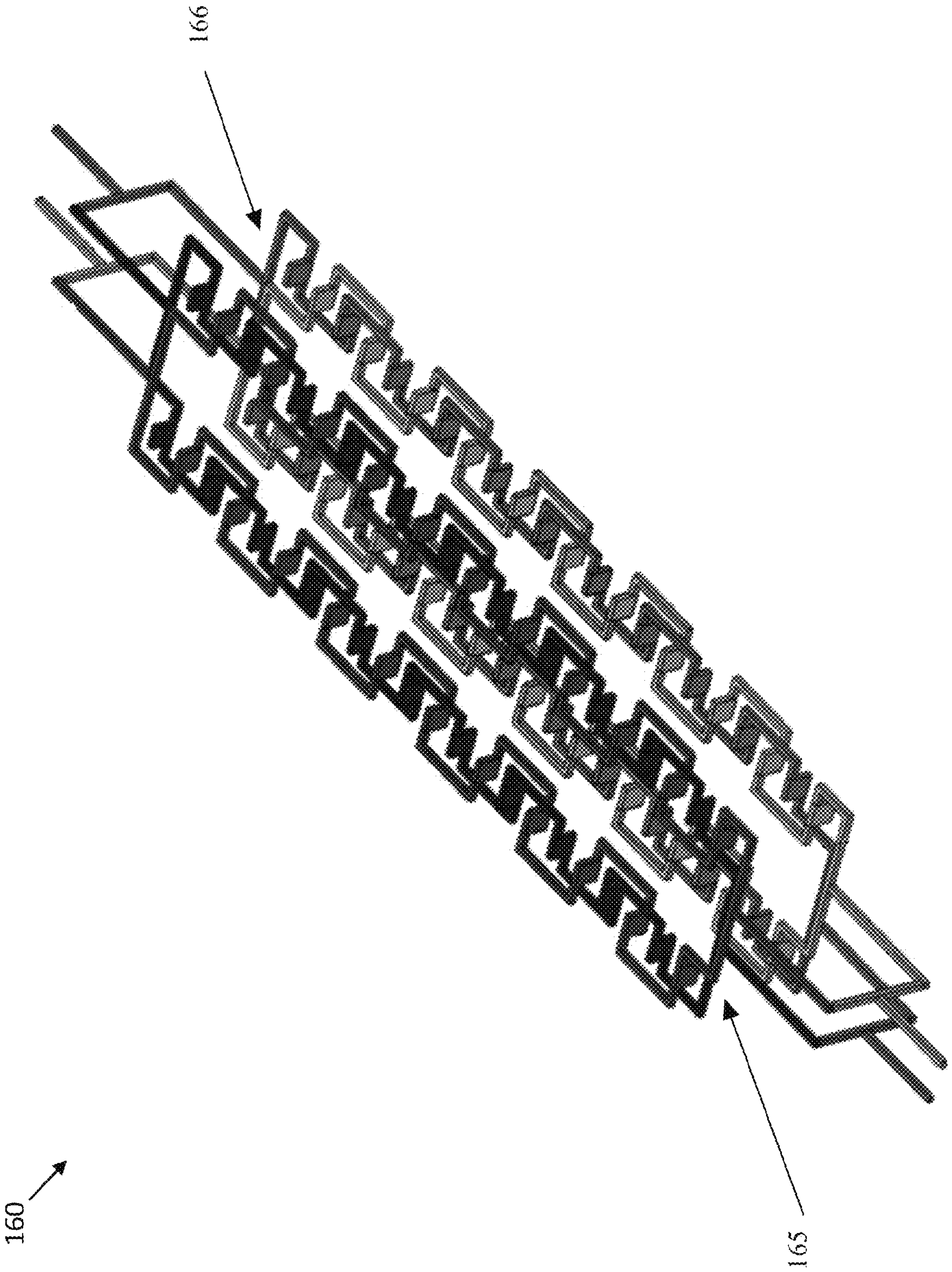

The structure in shown in FIG. 1C is ultimately a 2D array. This should be expanded in a scalable fashion to 3D. One of the ways to do so is to expand the array by binary tree in 2D first, to a number N of parallel fibers lying in the same horizontal plane, where N is equal to a power of 2 (not shown). Then, the plane can be arrayed vertically and connected by an analogous but vertical binary tree, to produce a N×N fiber bundle. Another way to go to 3D arrays is shown in FIG. 1D. First pair of artificial muscle fibers 165 may be arrayed vertically with second pair artificial muscle fibers 166 and connected by binary tree, producing a 2×2 fiber bundle 160. That bundle itself can then be arrayed first vertically then horizontally etc., in a binary fashion.

There are tradeoffs in the two bundling techniques. On the upside, the first method should have most of the cross-tendon vascularity limited to parallel planes, which leaves the tendon likely stronger overall. On the downside, the first method has far fewer vertical connections, which runs a higher risk of single-point failures disabling large subsections of the overall array. Conversely, the second method 140 distributes the cross-tendon vascularity in both lateral directions, likely weakening the tendon to a greater extent, but the more distributed vascularity would be more resistant to single-point failures.

Because the output force density would scale as the inverse square of the plate separation within each microcapacitor, it would pay to make that separation as small as possible while still avoiding dielectric breakdown. Hence, in practice the plates would be arranged far denser than depicted in FIGS. 1A-D wherein they are spaced out to improve visualization. Simultaneously, the connecting channels in the double helix would be far shorter than depicted in FIGS. 1A-D, thereby offering far less fluidic resistance than the FIGURE would suggest. Finally, the coupling channels in the binary tree architecture could grow wider as they rise in hierarchy, to suppress the rise of overall fluidic resistance of the structure.

Artificial muscles based on microfluidics, arrayed microcapacitors, electrostatic forces, and 3D printing offer a great promise for a wide range of applications. Making those a reality requires a complex wiring scheme that should simultaneously satisfy a list of mechanical, microfluidic, electrical, and scaling requirements. Herein we have presented such a solution—an innovative practicable scalable double-helix weave architecture that satisfies all requirements. Hence, the embodiments herein are a major development towards practical implementation of artificial muscles.

FIG. 2 is an illustration of an artificial muscle fiber within bulk structural material. Artificial muscle fiber 200 may include microcapacitor stack that is formed from multiple microcapacitor plates 215A and 225A, first polarity input 213, second polarity input 223, first polarity output 214, second polarity ouput 224, and a bulk material 250. Bulk material 250 may be but should not be limited to a polymer or dielectric. Bulk material 250 may serves as a dielectric and the mechanical medium of force transfer. Bulk material 250 may surround the microcapacitor stack, provide structure, and serve as a tendon equivalent.

Embodiments of the invention may include a system of microfluidic channels, where the channels are arranged into artificial muscles fibers. Each muscle fiber can include two independent mutually-unconnected microfluidic channels entwining in a double helix weave and kept at opposite electrical polarity as shown in FIGS. 1A-1D.

In some embodiments, each helix in each fiber can be a single channel that includes a series of parallel microcapacitor plates connected with connecting channels, where each rectangular (or square) plate is connected to its two neighbors in the same helix by corresponding opposite corners, e.g. from the bottom left corner through the plate to the top right corner of the same plate, to the top right corner of the next plate through that plate to its bottom left corner, etc. The arrangement of the channels ensures easy loading with liquid or gel conductor, avoidance of fluidic shunts, bubbles, and other defects.

In some embodiments, one helix uses the bottom left and top right corners of its plates for inter-plate connections within the same helix, while the other helix uses the top left and bottom right corners of its plates for the same purpose.

In some embodiments, the artificial muscle fibers are arranged in parallel with the longitudinal direction of the overall muscle, in a two-dimensional array where the fibers are arrayed in a horizontal plane and connected with one another in pairs by the same polarity, then the pairs are connected in pairs by the same polarity, etc., in a binary tree arrangement, where the number of fibers is N where N is a power of base 2, thereby producing only two inputs and two outputs to the whole array, regardless of the number of fibers in the two-dimensional array. The arrangement of the two-dimensional array is constructed to avoid dead ends, bubbles, and defects in the fluidic loading of the channels with liquid or gel conductor. Further, a goal the two-dimensional array is to ensure the same fluidic resistance along any specific pathway from input to output, ensuring symmetric vascularity, to ease loading and prevent shunts.

In some embodiments, two-dimensional arrays as described above can be arranged into an M number of planes of fiber arrays constructed that are arrayed vertically as stacks of fiber arrays, where the stacks are connected in adjacent pair by same polarity, then the pairs are connected in pairs, etc., following a binary tree architecture, where M is a power of 2, thereby producing a three-dimensional array of artificial muscle fibers, called a muscle fiber bundle. There are only two inputs and two outputs to the whole muscle fiber bundle regardless of the actual values of the parameters M and N. In some cases, M is equal to N and both are a power of 2. This arrangement of arraying maximizes the mechanical strength of the bulk material acting as tendons of the artificial muscle, by minimizing lateral vascularity, i.e. the channels running in directions lateral to the longitudinal axis of the muscle fiber bundle.

In some embodiments, the basic unit of a fiber bundle is four adjacent fibers arranged in parallel to the longitudinal axis of the muscle and bundle while also arranged in a 2×2 formation when viewed cross-sectionally, i.e. two fibers side-by-side horizontally on top and two fibers side-by-side horizontally on the bottom, wherein the matching polarities of the top pair are connected in pairs, just as the matching polarities of the bottom pair are also connected in pairs, and finally the matching polarities of the two pairs are also correspondingly connected in pairs, thereby producing a configuration wherein the 2×2 fiber bundle has only two inputs and two outputs regardless of the length of the bundle.

The fiber bundle described above can itself be arrayed first in the horizontal then in the vertical direction by iterative doubling, e.g. one unit bundle doubles to two horizontal unit bundles, connected in pairs by matching polarity, then the pair is doubled vertically to produce a 2×2 array of bundles, also connected in pairs by polarity, followed by horizontal doubling, etc., thereby alternating the direction of the doubling with each doubling, to produce a fractal architecture of arbitrary size and matching pair-wise connectivity. This bundle arraying maximizes the resilience of the structure to defects, at the expense of additional lateral wiring, i.e. increased lateral vascularity, that may decrease the strength of the tendon compared to the stacks of two-dimensional arrays described above.

In some cases, the fiber bundles may be of variable size of power of base 2, as lateral direction is alternated, to adjust and optimize the strength of the tendon versus the resilience of the structure to defects. There may be P number of fibers, where P is a power of 2, that are arrayed in one lateral direction, e.g. horizontal, then fractally connected accordingly in the same plane. This structure of P fibers can then be arrayed Q times along the orthogonal lateral direction, e.g. vertical, wherein Q is a power of 2, to adjust and optimize the strength of tendon versus defects resilience, e.g. with values of (P,Q) of (2,2), (4,4), (8,8), (16,16), (2,4), (2,8), (2,16), (4,8), (4,16), (8,16), etc. The resulting bundle can itself be arrayed by the same multiplicities in alternating lateral dimensions, to allow for array growth to arbitrary size.

This description provides exemplary embodiments of the present invention. The scope of the present invention is not limited by these exemplary embodiments. Numerous variations, whether explicitly provided for by the specification or implied by the specification or not, may be implemented by one of skill in the art in view of this disclosure.

It is to be understood that the above-described arrangements are only illustrative of the application of the principles of the present invention, and it is not intended to be exhaustive or limit the invention to the precise form disclosed. Numerous modifications and alternative arrangements may be devised by those skilled in the art in light of the above teachings without departing from the spirit and scope of the present invention.

What is claimed is:

1. An artificial muscle comprising:

an artificial muscle fiber comprising a first plurality of microfluidic channels of a first polarity and a second plurality of microfluidic channels of a second polarity, the first plurality of microfluidic channels and the second plurality of microfluidic channels are entwined in a double helix weave;

wherein the first polarity and the second polarity are electrically opposite charges;

a parallel array of artificial muscle fibers that comprises the artificial muscle fiber, the parallel array having the first plurality of microfluidic channels of each of the artificial muscle fibers are fluidically connected and the second plurality of microfluidic channels of each of the N artificial muscle fibers are fluidically connected; and wherein the parallel array is a power of base 2 so that only a first polarity input and a second polarity input of the artificial muscle fiber and a first polarity output and a second polarity output of the artificial muscle fiber are included in the parallel array.

2. The artificial muscle of claim 1, the first plurality of microfluidic channels further comprising a first plurality of parallel microcapacitor plates fluidically connected by the first plurality of microfluidic channels, wherein each microcapacitor plate is fluidically connected to a neighboring microcapacitor plate by diametrically opposed microfluidic channel.

3. The artificial muscle of claim 2, wherein the double helix weave facilitates loading of the microfluidic channels with a liquid or gel conductor and avoids fluidic shunts and bubbles.

4. The artificial muscle of claim 1, wherein the parallel array is configured to prevert dead ends, bubbles, and defects during fluidic loading of the first plurality of microfluidic channels and the second plurality of microfluidic channels with a liquid or gel conductor.

5. The artificial muscle of claim 1, wherein the first plurality of microfluidic channels and the second plurality of microfluidic channels have the same fluidic resistance from the first polarity input to the first polarity output and the second polarity input to the second polarity output.

6. The artificial muscle of claim 1, comprising a 3-dimensional M-by-M parallel array of N artificial muscle fibers, the M-by-M parallel array having the first plurality of microfluidic channels of each of the N artificial muscle fibers fluidically connected having the first polarity and the second plurality of microfluidic channels of each of the N artificial muscle fibers fluidically connected having the second polarity; wherein the M is a power of base 2 so that only a first polarity input and a second polarity input and a first polarity output and a second polarity output are included in the M-by-M parallel array of N artificial muscle fibers.

7. The artificial muscle of claim 6, where the Mis equal to the N.

8. The artificial muscle of claim 6, where the M-by-M parallel array of N artificial muscle fibers maximizes a mechanical strength of a bulk material acting as tendons of the artificial muscle.

9. The artificial muscle of claim 1, wherein multiple artificial muscle fibers are arranged in parallel into an artificial muscle fiber bundle, wherein the artificial muscle fiber bundle is configured with the first plurality of microfluidic channels of each of the artificial muscle fibers fluidically connected having the first polarity with a first polarity input and a first polarity output, and the second plurality of microfluidic channels of each of the artificial muscle fibers fluidically connected having the second polarity with a second polarity input and a second polarity output.

10. The artificial muscle of claim 9, further comprising an M-by-M array of muscle fiber bundles.

11. The artificial muscle of claim 10, wherein the M-by-M array of muscle fiber bundles increases lateral vascularity of the artificial muscle.

12. The artificial muscle of claim 1, wherein the artificial muscle fibers are arranged into a muscle fiber bundle, wherein the muscle fiber bundle comprises corresponding muscle fibers of a variable size of power of base 2 in an alternating lateral dimension.

13. The artificial muscle of claim 12, wherein a total number of the artificial muscle fibers is P, wherein the P is a power of 2, and wherein the artificial muscle fibers are arrayed in a first lateral direction and connected in the same plane, and wherein the artificial muscle fibers are arrayed Q times along an orthogonal lateral direction, wherein the Q is a power of 2.

14. The artificial muscle of claim 13, wherein the plurality of muscle fiber bundles is arrayed with other pluralities of muscle fiber bundles in alternating lateral dimensions.

* * * * *